United States Patent
Rytz et al.

(10) Patent No.: US 11,602,596 B2
(45) Date of Patent: Mar. 14, 2023

(54) SAFETY-CRITICAL DRUG DELIVERY PARAMETER DETERMINATION

(71) Applicant: Ypsomed AG, Burgdorf (CH)

(72) Inventors: Bernhard Rytz, Zollbrueck (CH); Michael Rufer, Luesslingen (CH); Stefan Lindegger, Huttwil (CH)

(73) Assignee: Ypsomed AG, Burgdorf (CH)

( * ) Notice: Subject to any disclaimer, the term of this patent is extended or adjusted under 35 U.S.C. 154(b) by 327 days.

(21) Appl. No.: 16/861,408

(22) Filed: Apr. 29, 2020

(65) Prior Publication Data
US 2020/0254176 A1    Aug. 13, 2020

Related U.S. Application Data

(63) Continuation of application No. PCT/IB2018/058198, filed on Oct. 22, 2018.

(30) Foreign Application Priority Data

Oct. 31, 2017 (EP) .................................... 17199304

(51) Int. Cl.
*A61M 5/172* (2006.01)
*G16H 40/63* (2018.01)
(Continued)

(52) U.S. Cl.
CPC .......... *A61M 5/1723* (2013.01); *A61M 5/172* (2013.01); *G16H 20/17* (2018.01);
(Continued)

(58) Field of Classification Search
CPC .. A61M 5/1723; A61M 5/172; A61M 5/5086; A61M 5/16827;
(Continued)

(56) References Cited

U.S. PATENT DOCUMENTS

| | | | |
|---|---|---|---|
| 9,552,052 B2* | 1/2017 | Bernstein | G06F 1/3287 |
| 2005/0145010 A1* | 7/2005 | Vanderveen | A61M 5/5086 73/1.57 |

(Continued)

FOREIGN PATENT DOCUMENTS

| | | |
|---|---|---|
| EP | 3476417 A1 | 5/2019 |
| WO | 2015100340 A1 | 7/2015 |

(Continued)

OTHER PUBLICATIONS

Pajic et al., Model-Driven Safety Analysis of Closed-Loop Medical Systems, 14 pages (Year: 2012).*

(Continued)

*Primary Examiner* — Thuy Dao
(74) *Attorney, Agent, or Firm* — Dorsey & Whitney LLP

(57) ABSTRACT

The safety and reliability of drug delivery systems are improved by the use of smartphones for calculating safety critical delivery parameters. A drug delivery device is adapted to perform a drug delivery operation based on an unconfirmed drug delivery instructions determined by a processing unit of a control device by applying a basic mathematic operation to control device input data. The drug delivery device comprises a communication module to receive, from the control device, the basic mathematic operation and the control device input data, and a redundancy module to determine a redundant drug delivery instructions by applying the basic mathematic operation to the control device input data received from the control device. The drug delivery device is adapted to prevent execution of the drug delivery operation if the unconfirmed drug delivery instructions and the redundant drug delivery instructions are found, by a comparator module, to conflict.

20 Claims, 2 Drawing Sheets

(51) Int. Cl.
*G06F 9/445* (2018.01)
*G06F 9/455* (2018.01)
*G16H 20/17* (2018.01)

(52) U.S. Cl.
CPC ..... *G16H 40/63* (2018.01); *A61M 2205/3584* (2013.01); *A61M 2205/50* (2013.01); *A61M 2230/20* (2013.01); *A61M 2230/201* (2013.01); *A61M 2230/63* (2013.01)

(58) Field of Classification Search
CPC ...... A61M 2205/3584; A61M 2205/50; G16H 20/17; G16H 40/63
See application file for complete search history.

(56) References Cited

U.S. PATENT DOCUMENTS

| | | |
|---|---|---|
| 2008/0059016 A1 | 3/2008 | Mayhew et al. |
| 2008/0306443 A1 | 12/2008 | Neer et al. |
| 2015/0182695 A1 | 7/2015 | Rosinko |
| 2015/0201880 A1 | 7/2015 | Bureau et al. |
| 2015/0251839 A1 | 9/2015 | Denny et al. |
| 2015/0290396 A1 | 10/2015 | Nagar et al. |
| 2015/0328411 A1 | 11/2015 | Friedman |
| 2016/0074587 A1 | 3/2016 | Searle et al. |
| 2016/0213848 A1 | 7/2016 | Whalley et al. |
| 2020/0261654 A1 | 8/2020 | Kühni et al. |

FOREIGN PATENT DOCUMENTS

| | | |
|---|---|---|
| WO | 2016033507 A2 | 3/2016 |
| WO | 2016041863 A1 | 3/2016 |
| WO | 2017132577 A1 | 8/2017 |
| WO | 2019077482 A1 | 4/2019 |
| WO | 2019087000 A1 | 5/2019 |
| WO | 2019087001 A1 | 5/2019 |

OTHER PUBLICATIONS

International Search Report and Written Opinion received for International Application No. PCT/IB2018/058198, dated Jan. 29, 2019, 10 pages.
International Preliminary Report on Patentability received for International Application No. PCT/IB2018/058198, dated May 5, 2020, 8 pages.
International Preliminary Report on Patentability received for International Application No. PCT/IB2018/058200, dated May 5, 2020, 9 pages.
International Search Report and Written Opinion received for International Application No. PCT/IB2018/058200, dated Jan. 8, 2019, 13 pages.
Extended European Search Report received for European Patent Application No. 17199307.4 dated Jun. 5, 2018, 8 pages.

* cited by examiner

SAFETY-CRITICAL DRUG DELIVERY PARAMETER DETERMINATION

RELATED APPLICATIONS

This application is a continuation to International Patent Application No. PCT/M2018/058198, filed Oct. 22, 2018, which in turn claims priority to European Patent Application No. 17199304.1 filed on Oct. 31, 2017, each of which is incorporated by reference herein, in the entirety and for all purposes.

FIELD OF THE INVENTION

The present invention relates to drug delivery systems for delivering, administering, injecting, infusing and/or dispensing liquids comprising a medicament or active ingredient. It starts from drug delivery systems involving the use of smartphones for calculating safety critical delivery parameters.

BACKGROUND OF THE INVENTION

A variety of diseases exist that require regular treatment by subcutaneous administration of a medicament. By way of example, diabetes may be treated by administration of insulin with the help of delivery devices that may be handled by the patients themselves. Accordingly, devices that are capable of accurately and controllably delivering fluids are particularly useful in the medical field for administration or dispensing of a known amount of drug at predetermined intervals. One category of delivery devices includes infusion pumps that have been developed for the continual subcutaneous administration of insulin or other medicaments for patients suffering from type I or type II diabetes. An insulin pump delivers fast-acting insulin via an infusion line to a small infusion set attached to the skin. The infusion set includes either a Teflon® cannula or a small metal needle inserted through the skin for gradual absorption into the blood stream. On the other hand, tubeless patch pumps are directly applied to the skin and continuously deliver insulin through a short cannula on the bottom of the pump. Alternatively, the delivery device may be a variable-dose, generally elongate or pen-shaped injection device that is removed from the injection site after drug delivery, with a control module integrated in the injection device, or as part of an add-on or supplemental device detachably attached to the injection device.

Insulin pumps configured as portable infusion devices are often discretely located on or around a patient, such as beneath clothing or in a carrying pouch. Some infusion pumps are therefore adapted to be programmed by means of remote control devices without directly interacting with a user interface of the pump. The pump can be programmed or remote controlled to deliver basal insulin and give a bolus of insulin for a meal or high blood sugar. With the proliferation of handheld consumer electronic devices, such as smartphones, there is a desire to be able to utilize such devices as the remotely controlled device for remotely operating a delivery device. However, medical devices and consumer electronics have vastly different safety and reliability profiles, such that use of consumer electronic devices to program medical devices such as infusion pumps could present safety issues for the patient.

In safety critical systems, a safety critical value such as a proposed bolus amount and/or duration, may be computed in a redundant manner via two independent channels, requiring at least approximatively identical output by both channels and thus allowing at least to detect erroneous operation of a single channel. Known redundancy methods include hardware-redundant computation, including complete duplication and execution of a task or algorithm on different microprocessors, or in different cores of a single processor. On the other hand, diverse redundancy uses different number formats to enforce independent calculations on a single microprocessor, and may include integers being processed in an Mathematic Logic Unit (ALU), and floating point numbers being processed in a Floating Point Unit (FPU). Alternatively, ALU operators may be tested for fault free operation by means of test vectors with known outcome, which allows to detect erroneous behavior due to hardware malfunctioning.

With common consumer electronic devices including smartphones and handheld tablet devices, the above methods may not always be available. Duplication of computer processors is generally out of scope, and redundant calculations on two different cores of a multi-core processor may not be guaranteed. Furthermore, diverse redundancy calculations are not ensured either, as floating point operations may be executed by virtue of the ALU. Ultimately, test vector evaluation and subsequent calculations may be executed on different cores. Testing of ALU operators in common consumer electronic devices is further complicated by missing assembler instructions or processor specific instructions, and by the fact that a same operating system may be used with distinct processors.

WO2016/041863 A1 discloses a supervising entity or safety module as part of, or separate from, a mobile device, for testing whether the mobile device is functional and free of errors, e.g., as introduced by viruses or updates of the operating system. Correct solution of a validation problem in the form of a simple mathematical operation with given starting values as solved by the mobile device is checked by the testing module.

WO 2015/100340 discloses a system for enhanced reliability and safety of programming and/or operating an infusion pump, including a remote control device such as a mobile phone. A safety processor acts as an intermediary device between the mobile phone and the infusion pump to review transmissions from the mobile phone prior to the transmissions being delivered to the infusion pump. Specifically, a programming operation for the infusion pump, performed by the smartphone, is transmitted to the safety processor as a request for an operation on the infusion pump. The safety processor reviews the request and determines if it is acceptable or plausible, based on the parameters related to operation of the medical device stored in the memory. The safety processor may receive information from a Continuous Glucose Monitor (CGM), and determine whether it is permissible to execute the operating instructions on the medical device by utilizing the information from the CGM.

So called closed loop or artificial pancreas algorithms as disclosed for instance in WO 2017/132577 may be used to track the blood sugar or glucose level of a person and the insulin doses delivered in order to determine when the person needs additional administration of insulin. The system does prompt the person to administer a certain dose of insulin upon determination that the latter is required to control his/her blood sugar, based on current and/or forecast uncontrolled blood sugar level. The amount of insulin may be determined involving a correction factor or insulin sensitivity factor of the user which governs how much insulin is needed to lower the blood sugar level of the user by one unit. Accordingly, in a simple implementation the following relationship is used to determine an amount of insulin needed:

$$\text{Insulin needed} = \text{current blood sugar/correction factor} - \text{insulin on board}$$

Here, the insulin on board corresponds to previously administered insulin doses not yet completely absorbed into the blood stream. Alternatively or in addition, a so-called bolus calculator may determine an insulin bolus dose amount based on glucose information including the most recent glucose level reading and historical glucose trend information, patient weight, and an exercise factor of the patient, in order to cover the amount of carbohydrate of a planned or ingested meal according to the following relationship:

$$\text{Insulin bolus} = \text{grams of carbohydrate/carbfactor.}$$

Here, the carbfactor or insulin-to-carbohydrate ratio of the patient indicates the number of grams of carbohydrate that one unit of fast acting insulin may cover.

SUMMARY OF THE INVENTION

It is an objective of the invention to increase safety and reliability of adaptable drug delivery systems involving the use of common consumer electronic devices for calculating safety critical delivery parameters. This objective is achieved by a method of confirming a drug delivery method of operation, a drug delivery system, and a computer program product according to the claims.

According to an implementation of the invention, a safety-critical drug delivery operation or task to be performed or executed by means of a drug delivery device is based on a drug delivery command or instruction received via a communication interface of the delivery device. The drug delivery instructions may include a delivery parameter such as a bolus amount and/or duration, a basal rate, a delivery time or interval, or a binary signal triggering instantaneous delivery of a predefined dose. The drug delivery instructions received by the delivery device and/or the resulting drug delivery operation are safety- or health-critical in the sense that any instructions deviating significantly from the intended instructions, for instance by specifying an erroneous bolus amount and/or duration or a delayed delivery time, may have severe consequences for the health of the patient. The drug delivery operation and/or the drug delivery instructions are confirmed or validated according to the following steps:

1. Determining, or computing, by a remote control device different from the delivery device and independent from other drug calculations, an unconfirmed drug delivery instructions by applying a basic mathematic operation, or the corresponding operator, to control device input data. The basic mathematic operation may include any of adding, subtracting, multiplying, or dividing two input data values. The control device input data may include first input data indicative of a most recently consumed, or of an imminent, amount of carbohydrate, input manually into the control device by the patient. The input data may include first input data indicative of a blood glucose level of the patient as determined and transmitted by a Blood Glucose Monitoring (BGM) device. The control device input data may also include second input data including stored medical data of the patient, including patient weight, insulin to carbohydrate ratio, correction factor, and exercise factor of the patient, and historical data indicative of a drug delivery history previously input into, or read by, the control device. The control device is a common consumer electronic device, which excludes approved dedicated medical control devices but includes stationary and, preferably, mobile devices not conforming to medical safety standards, such as smartphones, handheld tablet devices, or any other portable or wearable smart gadgets with user interfaces.

2. Communicating, by the control device and by wireless transmission, the basic mathematic operation and the control device input data to a redundancy or safety co-processing module or confirmatory unit implemented on, or hosted by, a redundancy device that is different from the control device and including a communication interface adapted for receiving the communication from the control device.

3. Determining, by the redundancy module, a redundant drug delivery instruction based on the basic mathematic operation and the control device input data as received from the control device. To this purpose, the redundancy module may provide for an at least rudimentary and preferably standardized mathematical calculations.

4. Comparing, by a comparator module or unit preferably incorporated in the redundancy device and/or in the control device, the unconfirmed drug delivery instruction and the redundant drug delivery instruction, and preventing, in case of conflicting instructions, transmission, reception, and/or execution of the safety-critical delivery operation by the delivery device. On the other hand, at least approximately matching unconfirmed and redundant drug delivery instructions are considered safe, and the drug delivery operation is executed by the delivery device, preferably without any further confirmation on the correctness of the delivery instructions.

By way of example, the control device input data and the basic mathematic operator may be provided to the redundancy device in Reverse Polish Notation (RPN). The result of a first basic mathematic operation may further be operated on by applying or executing another basic mathematic operation. A sequence of suitably prioritized, or bracketed, basic mathematic operations may thus represent any analytical formulae. Communication from the control device to the redundancy module in this case may include a plurality of basic operators, and more than two control device input data values. On the other hand, the basic mathematic operators of the basic calculations may be complemented by logical, comparative, control flow and/or Boolean operators. The aforementioned basic mathematic operators may thus be combined into more complex algorithms and control flows. Accordingly, an extended service interface of the redundancy module may include a set of operators or instructions supportive of a variety of data types and enabling more flexible computations beyond analytical formulae and including algorithms and control flows.

The redundancy device may provide the above calculations on behalf of more than one client. In particular, in addition to the control device, a Continuous Glucose Monitor (CGM) may likewise request a mathematical computation, not necessarily redundant, to be executed on its behalf, such as a statistical function, including a mean value, of several consecutive CGM readings.

Upon availability of a confirmed delivery instructions at the drug delivery device, the drug delivery device may be operated manually by the patient activating a trigger button to start delivery, or even providing mechanical power to drive delivery of a dose set automatically based on the drug delivery instruction. However, the drug delivery device may be a subcutaneous infusion device such as an insulin pump including a power source for automated delivery not requiring further human intervention.

The wireless communication between the control device and the redundancy module may require suitable transceiver units for short or near range wireless communication at both devices. Preferably, such communication is established according to the Bluetooth Low Energy (LE) Core Specification, or any equivalent near range communication technology with application level security including RFID (Radio Frequency Identification), NFC (Near-Field Communication), ANT (Adaptive Network Technology), Zigbee (IEEE 802.15.4 based, low power, low data rate supporting wireless networking standard), WAN (Wide Area Network), WLAN (Wireless Local Area Network), LORA (Long Range) or the like, which in turn may cover the encryption, trust, data integrity and privacy of the communication. Corresponding features include advanced out-of-band pairing where the control device and the redundancy device involved in the communication exchange their identity information to set up trust and get the encryption keys ready for the future data exchange, or the ability to send authenticated data over an unencrypted transport between two devices with a trusted relationship. The near range wireless communication from the control device may be directed to a medical gateway device and complemented by an internet connection from the gateway device to a redundancy module on a remote service provider. The redundancy module may be implemented on a redundancy device, such as a second mobile device, with similar computational configurations as the remote control device, or on a dedicated remote server. However, the redundancy module or the corresponding calculation is preferably implemented on, or hosted by, the delivery device itself. The delivery device, such as an insulin pump, by its very nature, responds to medical safety standards, and as part of the delivery system is readily available without the need for any further communication link to be established.

In implementations and alternatives, the redundant drug delivery instruction is communicated from the redundancy module to the control device. The comparator module implemented on the control device then proceeds to comparing the unconfirmed and redundant drug delivery instructions, and finally communicates either of the two matching delivery instructions to the delivery device. Alternatively, the comparator module is implemented on the redundancy device, to compare the unconfirmed drug delivery instructions received from the control device and the redundant delivery instructions calculated by the redundancy module of the redundancy device. The redundancy device finally communicates either of the two matching delivery instructions to the drug delivery device. Mixed or conflated embodiments with comparator modules at both the control device and the redundancy device are also possible.

In implementations and alternatives, a token such as a time-stamp or other unique identifier is used to enable identification and subsequent comparison of corresponding unconfirmed and redundant delivery instructions in respective instruction sequences generated independently. As the unconfirmed and redundant delivery instructions reach the comparator module via distinct paths, an intended order may not be respected, and the token may help to unambiguously unite the instructions pertaining to the same mathematic operation and control device input data.

In implementations and alternatives, the token is generated by the control device, and communicated together with, or otherwise linked to, the mathematic operation and the input values to the redundancy module. The redundant delivery instruction is stored in a log or result list of a storage module of the redundancy device together with the token. Alternatively, the token is generated by the redundancy module, and stored together with the redundant delivery instruction in a log of a storage module of the redundancy device. In parallel, the token is communicated to the control device as a response to the communicated basic mathematic operation and data values. In such embodiments, the token is subsequently communicated together with the unconfirmed instructions by the control device to the comparator module implemented on the redundancy device, and thus having access to the result list for identifying and retrieving the previously stored redundant delivery instructions.

According to another implementation, provided is a drug delivery system with a delivery device adapted to execute a safety-critical task based on an unconfirmed result determined at a remote processing unit of a control device by applying an operator (e.g., mathematic operator) to control device input data. The drug delivery device comprises a communication module to receive, from the control device, the operator and the control device input data, and a redundancy module to determine a redundant result by applying the operator to the control device input data received from the control device. The drug delivery device is adapted to prevent execution of the safety-critical task if the unconfirmed result and the redundant result are found, by a comparator module, to conflict. The operator is one of an mathematic, logical, comparative, control flow and/or Boolean operator, and the result is preferably determined by suitably processing or combining two or more input data values according to the operator. Alternatively, the result may also be obtained from a single input data value, such as by applying a rounding rule. The control device input data and the result may include a system status such as an alarm or error status or an activated status of the delivery device.

The operator may be a basic mathematic operator for any of adding, subtracting, multiplying, or dividing two input data values. The control device input data may include first input data indicative of a most recently consumed, or of an imminent, amount of carbohydrate, input manually into the control device by the patient. The input data may include first input data indicative of a blood glucose level of the patient as determined and transmitted by a Blood Glucose Monitoring (BGM) device. The control device input data may also include second input data including stored medical data of the patient, including patient weight, insulin to carbohydrate ratio, correction factor, and exercise factor of the patient, and historical data indicative of a drug delivery history previously input into, or read by, the control device.

According to further implementations, provided is a computer program product in the form of an application program stored on a computer-readable medium to be installed and run on a control device for controlling a drug delivery operation performed by means of a drug delivery device. The computer-readable medium may be a floppy disk, a hard disk, an USB (Universal Serial Bus) storage device, a RAM (Random Access Memory), a ROM (Read Only Memory), an EPROM (Erasable Programmable Read Only Memory), or a data communication network, e.g. the Internet, which allows downloading program code. The computer program causes, when being executed by a processor unit of the mobile control device, the processing unit to execute the steps of:

1. Determining an unconfirmed drug delivery instruction by applying a basic mathematic operation to control device input data;
2. Communicating the basic mathematic operation and the control device input data to a redundancy device;

3. Receiving, from the redundancy device, a redundant drug delivery instruction determined by a redundancy module of the redundancy device by applying the basic mathematic operation to the control device input data, and
4. Comparing the unconfirmed drug delivery instruction and the redundant drug delivery instruction, and preventing, in case of conflicting instructions, execution of the drug delivery operation by the drug delivery device.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

BRIEF DESCRIPTION OF THE DRAWINGS

Implementations of the present disclosure are explained in more detail in the following text with reference to exemplary embodiments as illustrated in the attached drawings, of which.

For consistency, the same reference numerals are used to denote similar elements illustrated throughout the drawings.

DETAILED DESCRIPTION OF PREFERRED EMBODIMENTS

Figure 1:
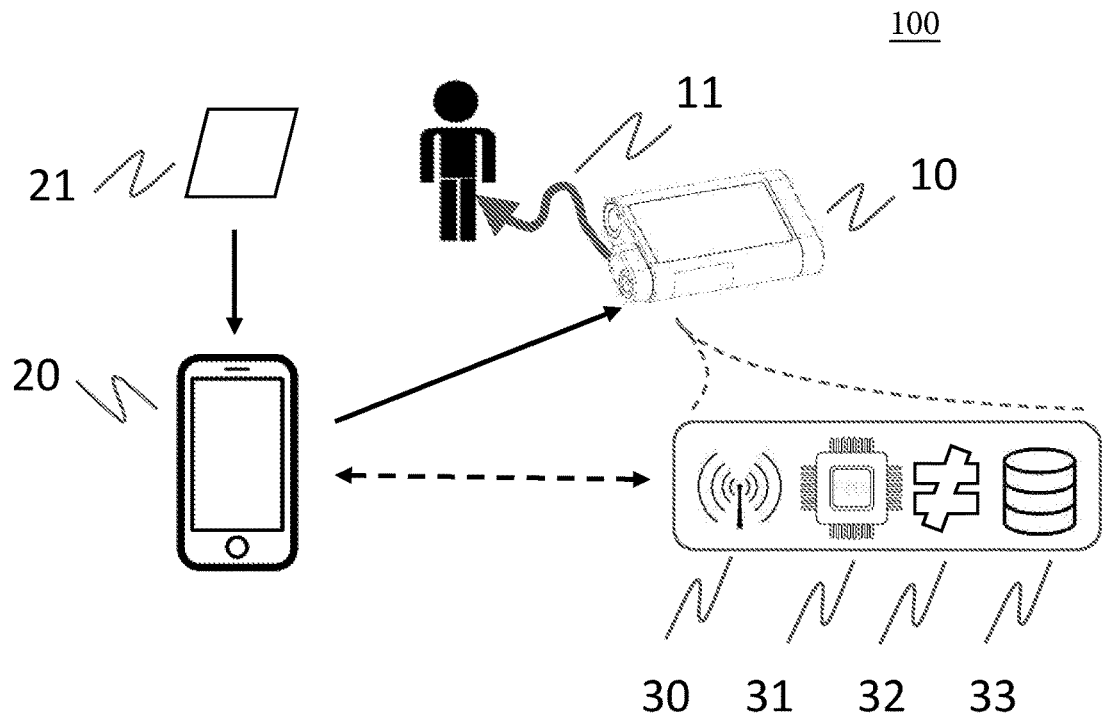
FIG. 1 depicts a medical drug delivery and patient support system according to implementations of the present disclosure.

FIG. 1 depicts an exemplary medical drug delivery and patient support system 100, with a patient receiving doses of medication on a regular basis from a drug delivery device 10 through a flexible tube or a cannula 11. A remote mobile control device 20 such as a smartphone or tablet device running a dedicated application program is provided with control device input data 21. The control device 20 determines an unconfirmed drug delivery instruction intended to control a safety critical operation of the delivery device 10. In order to increase confidence in the drug delivery instruction, the control device 20 is adapted to communicate with a communication module 30 which in turn serves as an interface to a redundancy, or redundant computation, module 31, a comparator module 32, and/or a storage module 33. In FIG. 1, the latter modules 31, 32, 33 are all assigned to, or implemented on, the drug delivery device 10, but nevertheless may be allocated to, and hosted by, distinct devices of the system 100 as will be apparent from the following disclosure.

The control device 20 includes a user interface to receive control device input data 21, either entered manually or input via suitable communication means from another device, and/or memory means from which previously stored control device input data 21 may be retrieved. The input data 21 may include user data such as patient weight, insulin to carbohydrate ratio, correction factor, and exercise factor. The control device 20 is adapted to send commands or instructions to the delivery device 10. The instructions include a dose amount and/or a dose timing, determined by taking into account glucose level and trend, and other factors. The control device 20 may be in continuous communication with a glucose monitor and the delivery device 10 to provide for near real-time adjustments in glucose treatment. Glucose data, insulin injection data, and other relevant data may be stored and accessible to interested or permitted parties either locally through the user interface of the control device, or globally via remote servers or databases.

Figure 2:
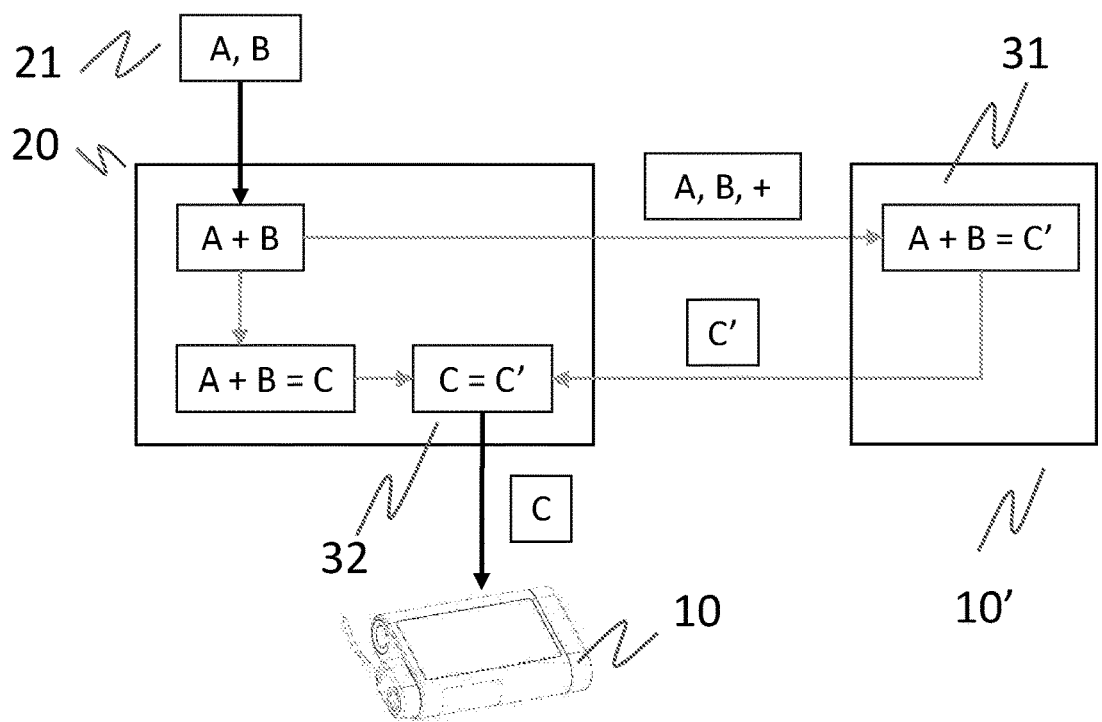
FIG. 2 illustrates a schematic of a method of confirming a drug delivery instruction and a corresponding configuration of the devices of the medical drug delivery system according to implementations of the present disclosure.

FIG. 2 illustrates a method of confirming a drug delivery instructions and a corresponding configuration of the devices of the medical drug delivery system 100 of FIG. 1, according to implementations of the present disclosure. A control device 20 has access to control device input data 21 including two parameter values A, B. The safety critical calculation to be performed being "A plus B", suitable processing capability of the control device 20 determines an unconfirmed delivery instruction or instruction C. In parallel, the input data A, B as well as the operator "plus" are forwarded to a redundancy module 31 on a redundancy device 10', and a redundant delivery instruction C' is calculated by the redundancy module 31. The redundant delivery instruction C' is returned to the comparator module 32 of the control device 20, and upon successful validation by the comparator module 32, either of the unconfirmed instruction C or the redundant instruction C' is forwarded by the control device 20 to the delivery device 10. The redundancy device 10' and the delivery device 10 may be the same device, and such forwarding may be limited to an indication about the successful validation of the redundant instruction C', such that the latter may be shared device-internally with a delivery controller of the drug delivery device 10. Incidentally, either the control device 20 or the redundancy module 31 may proceed to a plausibility check based on the physical units of the input parameters A, B, and for instance abort the process if two input parameter values with distinct units are to be summed.

Figure 3:
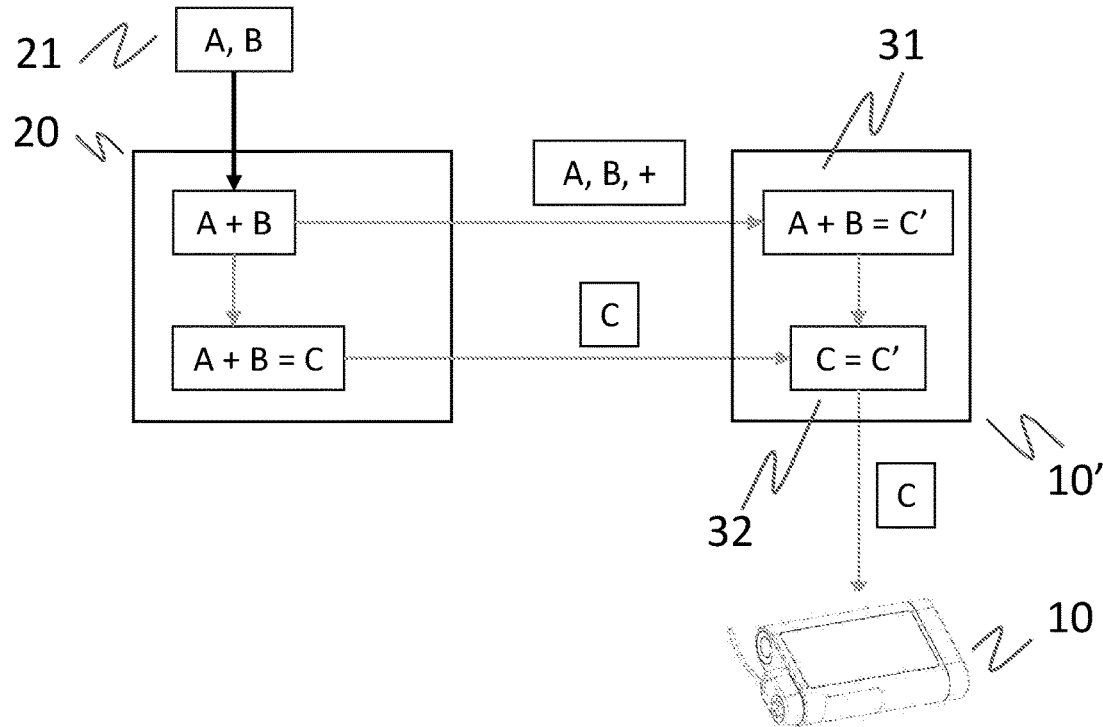
FIG. 3 illustrates a schematic of a second method of confirming a drug delivery instructions and a corresponding configuration of the devices of the medical drug delivery system according to implementations of the present disclosure.

FIG. 3 differs from FIG. 2 to the extent that the comparator module 32 is arranged on the redundancy device 10', and in that the unconfirmed delivery instruction C is communicated to the redundancy device 10' for the purpose of comparison. Upon successful validation by the comparator module 32, either of the unconfirmed instruction C or the redundant instruction C' is forwarded to the delivery device 10. Where the redundancy device 10' and the delivery device 10 are located on the same device, such forwarding may be limited to a device-internal sharing of the delivery instruction with a delivery controller of the drug delivery device.

In FIG. 3, the unconfirmed delivery instruction and the input data values are assigned an instruction identifier or functional designation in the form of a simple tag indicative of the instruction type inherent to, or associated with, the unconfirmed instruction C, such as "instantaneous bolus". Using a simple instruction type identifier is based on the assumption that there is a sufficient pause between successive instructions of the same type or designation to prevent mixing of successive instructions. The instruction type identifier then allows the comparator module 32 to proceed to a further plausibility check, and to abort the process in case the instruction type of the unconfirmed instruction does not match the instruction type identifier of the redundant instruction C'.

Figure 4:
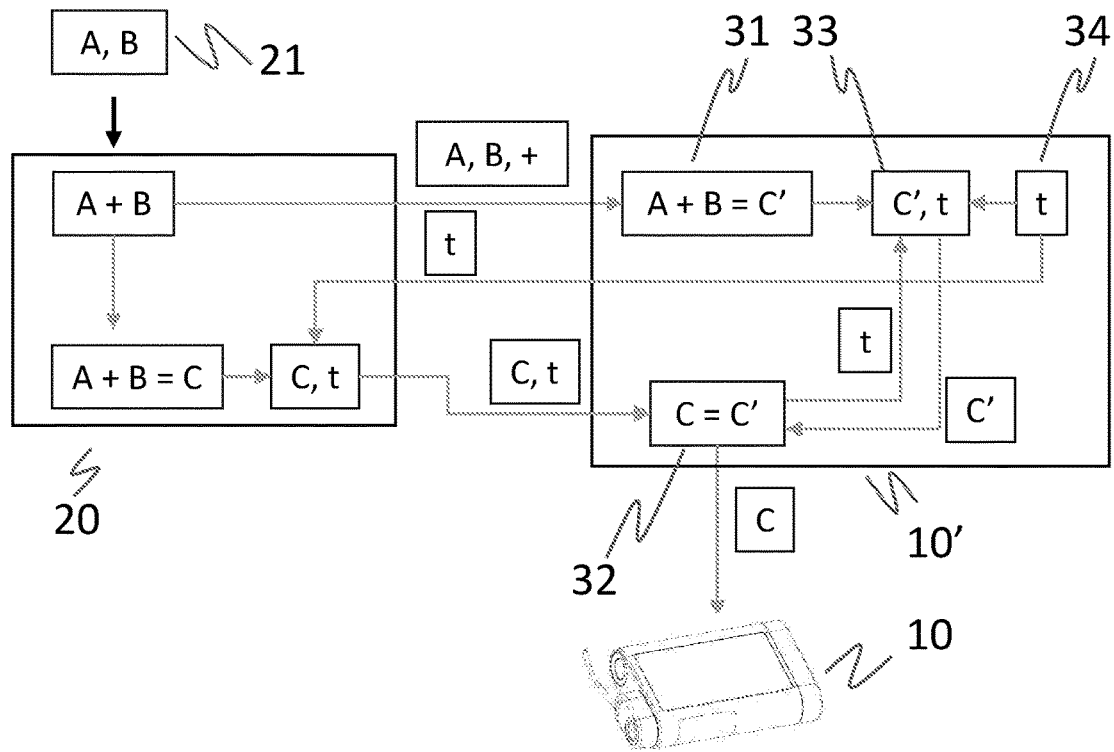
FIG. 4 illustrates the second method complemented by the use of a token.

FIG. 4 illustrates the variant of FIG. 3, complemented by the use of a token in order to unambiguously identify corresponding delivery instructions. In this case, a token "t" is generated by or on behalf of the redundancy module 31 by a token generator 34, and stored together with the redundant delivery instruction C' in a result list of a storage module 33 of the redundancy device 10'. In parallel, the token t is communicated to the control device 20 as a response to the previously communicated basic mathematic operation and data values, as indicated by the connector pointing from right to left in FIG. 4. The token t is ultimately communicated together or in parallel with the unconfirmed delivery instruction C by the control device 20 to the comparator module 32 likewise implemented on the redundancy device 10'. The comparator module 32 has access to, or is provided with, the result list for identifying and retrieving therefrom the previously stored redundant delivery instruction C' based on the token t. A token may also be employed in connection with other variants, such as the one depicted in FIG. 2.

In order to further increase reliability of the process, the token introduced above may be provided with a timeout property, may include a suitably increment to ensure single usage at least during a suitably defined process cycle, and/or may be encrypted or hashed. Furthermore, a token may be indicative of, or linked to, a type of the delivery instruction, such that, e.g., "instantaneous bolus" type instructions are incremented separately. Token t and corresponding delivery instruction C may be eliminated from the result list upon initial identification, but may also be stored for an extended period of time. In the latter configuration, instruction C may be retrieved at a later time, as input data for a subsequent iterating calculation, which has the potential of saving processing power at both the control device and the redundancy device. To that purpose, a token table maintained by the token generating entity, or any other set of identifiers indicative of previous calculations, may prove helpful.

While the invention has been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims shall not preclude the existence of further meaningful combinations of these elements or steps.

What is claimed is:

1. A drug delivery system, comprising:
    a control device adapted to determine an unconfirmed result by applying an operator to control device input data;
    a delivery device adapted to perform a drug delivery operation, and adapted to execute a safety-critical task based on the unconfirmed result, wherein the delivery device has a communication module to receive the operator and the input data from the control device, and wherein the delivery device has a redundancy module to determine a redundant result by applying the operator to the input data received; and
    a comparator module for comparing the unconfirmed result determined by the control device and the redundant result, wherein execution of the safety-critical task is prevented if the unconfirmed result and the redundant result are found to conflict.

2. The drug delivery system of claim 1, wherein the redundant result is a drug delivery instruction determined by applying a basic mathematic operation to the control device input data, and wherein the safety-critical task is the drug delivery operation.

3. The drug delivery system of claim 1, wherein the delivery device further comprises the comparator module, and wherein the communication module is adapted to receive, from the control device, the unconfirmed result.

4. The drug delivery system of claim 1, wherein the delivery device further comprises a storage module for storing a token generated by the redundancy module together with the redundant result,
    wherein the communication module is further adapted to:
        communicate the token to the control device as a response to the received operator and input data; and
        receive, from the control device, the unconfirmed result together with the token, and
    wherein the comparator module is adapted to identify the unconfirmed result and the redundant result based on the token.

5. The drug delivery system of claim 1, wherein the operator selected from:
    a basic mathematic operator for adding, subtracting, multiplying, or dividing;
    a sequence of prioritized or bracketed basic mathematic operators for adding, subtracting, multiplying, or dividing; or
    a combination of basic mathematic operators for adding, subtracting, multiplying, or dividing along with logical, comparative, control flow and/or Boolean operators.

6. A method of confirming a drug delivery operation to be performed by a drug delivery device, based on a drug delivery instruction received by the delivery device, comprising:
    determining, by a processing unit of a control device, unconfirmed drug delivery instructions by applying a basic mathematic operation to received data;
    communicating, by the processing unit, the basic mathematic operation and the received data to a redundancy module on a redundancy device;
    determining, by the redundancy module, redundant drug delivery instructions by applying the basic mathematic operation to the received data received from the control device; and
    comparing, by a comparator module, the unconfirmed drug delivery instructions and the redundant drug delivery instructions,
    wherein the comparator module prevents execution of the drug delivery operation by the drug delivery device when the unconfirmed drug delivery instructions and the redundant drug delivery instructions conflict.

7. The method of claim 6, wherein the redundancy device is the drug delivery device, and the drug delivery device is separate from the control device.

8. The method of claim 7, wherein the step of communicating, by the processing unit, the basic mathematic operation and the received data to the redundancy module is by Bluetooth, RFID, NFC, ANT, Zigbee, WAN, WLAN, LORA, or another near range communication technology with application level security.

9. The method of claim 7, wherein the comparator module is implemented on the drug delivery device, and causes the step of:
communicating, by the control device, the unconfirmed drug delivery instructions to the drug delivery device.

10. The method of claim 6, wherein the basic mathematic operation comprises one or more of:
adding, subtracting, multiplying, or dividing;
a sequence of prioritized or bracketed basic mathematic operations for adding, subtracting, multiplying, or dividing; or
a combination of basic mathematic operations for adding, subtracting, multiplying, or dividing along with logical, comparative, control flow and/or Boolean operators.

11. The method of claim 6, wherein the received data comprises one or more of user input data indicative of a most recently consumed, or of an imminent, amount of carbohydrate, data indicative of a blood glucose level of the patient as determined and transmitted by a Blood Glucose Monitoring device, or stored medical data of the patient.

12. The method of claim 11, wherein the received data comprises the stored medical data of the patient, and includes one or more of patient weight, insulin to carbohydrate ratio, correction factor, exercise factor of the patient, or historical data indicative of a drug delivery history previously input into, or read by, the control device.

13. The method of claim 6, wherein the comparator module is implemented on the processing unit of the control device, and causes the steps of:
communicating, by the redundancy module, the redundant drug delivery instructions to the control device; and
communicating, by the processing unit, the drug delivery instruction to the drug delivery device.

14. The method of claim 6, wherein the comparator module is implemented on the redundancy device, and causes the steps of:
communicating, by the processing unit of the control device, the unconfirmed drug delivery instructions to the redundancy device; and
communicating, by the redundancy device, the drug delivery instruction to the drug delivery device.

15. The method of claim 6, wherein the comparator module confirms the drug delivery operation by the drug delivery device when the unconfirmed drug delivery instructions and the redundant drug delivery instructions do not conflict.

16. The method of claim 6, further comprising the step of:
assigning a single token to both the unconfirmed drug delivery instructions and to the redundant delivery instructions; and
identifying, by the comparator module, the unconfirmed drug delivery instructions and the redundant delivery instructions based on the token.

17. The method of claim 16, wherein the comparator module is implemented on the redundancy device, and causes the steps of:
generating, by the control device, the token and communicating the token together with the basic mathematic operation and the received data to the redundancy module;
storing the redundant delivery instructions together with the token; and
communicating, by the control device, the token and the unconfirmed drug delivery instructions to the comparator module.

18. The method of claim 16, wherein the comparator module is implemented on the redundancy device, and causes the steps of:
generating, by the redundancy module, the token and storing the token together with the redundant drug delivery instructions;
communicating the token to the control device as a response to the communicated basic mathematic operation and data values; and
communicating, by the control device, the unconfirmed drug delivery instructions together with the token, to the comparator module.

19. A computer program product stored in a non-transitory computer-readable medium executed by a processing unit of a control device for controlling a drug delivery operation performed by means of a drug delivery device, wherein the computer program product causes the processing unit to execute the steps of:
determining unconfirmed drug delivery instructions by applying a basic mathematic operation to control device input data;
communicating the basic mathematic operation and the control device input data to a redundancy device;
receiving, from the redundancy device, redundant drug delivery instructions determined by a redundancy module of the redundancy device by applying the basic mathematic operation to the control device input data;
comparing the unconfirmed drug delivery instructions and the redundant drug delivery instructions; and
preventing, in case of conflicting instructions, execution of the drug delivery operation by the drug delivery device.

20. The computer program product of claim 19, wherein applying the basic mathematic operation comprises:
applying one or more of a sequence of prioritized or bracketed basic mathematic operations, the one or more basic mathematic operations comprising one or more of adding, subtracting, multiplying, or dividing, or
combining one or more basic mathematic operations with logical, comparative, control flow and/or Boolean operators.

* * * * *

UNITED STATES PATENT AND TRADEMARK OFFICE
CERTIFICATE OF CORRECTION

PATENT NO. : 11,602,596 B2
APPLICATION NO. : 16/861408
DATED : March 14, 2023
INVENTOR(S) : Bernhard Rytz, Michael Rufer and Stefan Lindegger It is certified that error appears in the above-identified patent and that said Letters Patent is hereby corrected as shown below:

In the Specification

In Column 1, Line 7, after Application No. delete ""PCT/M2018/058198"" and replace with --PCT/IB2018/058198--

Signed and Sealed this
Thirty-first Day of October, 2023

Katherine Kelly Vidal
Director of the United States Patent and Trademark Office